United States Patent [19]

Comparetto

[11] 4,150,675

[45] Apr. 24, 1979

[54] OSTEOTOME AND A METHOD OF SURGICALLY USING SAME

[76] Inventor: John E. Comparetto, 108 Cropper St., Chincoteague, Va. 23336

[21] Appl. No.: 763,623

[22] Filed: Jan. 28, 1977

[51] Int. Cl.² ............................................. A61B 17/32
[52] U.S. Cl. .................................... 128/305; 30/302; 30/316; 128/1 R
[58] Field of Search ............... 128/305, 310, 1 R, 2 B; 30/358, 277, 305, 301, 302, 303, 314, 315, 316; 83/669, 663

[56] References Cited

U.S. PATENT DOCUMENTS

| 2,053,777 | 9/1936 | Pekrol | 30/301 |
| 2,690,750 | 10/1954 | Steinberg | 128/305 |
| 3,127,939 | 4/1964 | Rink | 30/316 X |

FOREIGN PATENT DOCUMENTS 2457270  7/1976  Fed. Rep. of Germany ........... 128/305

*Primary Examiner*—Robert W. Michell
*Assistant Examiner*—Michael H. Thaler
*Attorney, Agent, or Firm*—Haight & Huard

[57] ABSTRACT

An osteotome includes an arcuate cutting blade portion and a planar cutting blade portion integrally secured thereto. The arcuate portion is defined from a locus of a perfect circle and is axially elongated relative to the planar blade so as to permit the arcuate blade to be reained within an initially cut portion of a bone while the entire osteotome is rotated to a new, second position in order to perform a second cutting of the bone. The two cuttings of the bone serve to remove a section of the original bone, and in this manner, when the bone sections are repositioned relative to one another, the same will be precisely aligned so as to correct the original bone deformity. The arcuate portion also includes a stepped portion so as to facilitate the rotational positioning of the osteotome in either direction to the second position relative to the first position, and various indicating devices can also be provided so as to visually indicate the precise amount the instrument is to be rotated between the cutting positions.

10 Claims, 14 Drawing Figures

OSTEOTOME AND A METHOD OF SURGICALLY USING SAME

BACKGROUND OF THE INVENTION

1. Field of the Invention

The present invention relates generally to surgical instruments, and more particularly to a new and improved osteotome.

2. Description of the Prior Art

Many bone deformities in the human foot lend themselves to correction by means of surgical procedures. For example, in the instance of improper formation, angulation, or orientation of a particular bone with respect to other bones or components of the foot, the surgical procedure normally involves the removal of a wedge-shaped section of the malformed or misaligned bone at a predetermined location and the relative repositioning of the remaining bone sections so as to impart to the surgically corrected bone the proper relative configuration or orientation. The wedge-shaped section removed from the original bone is, of course, of a predetermined size which naturally depends upon the extent of the correction required.

It has been found that the formation of the wedge-shaped sections, in compliance with preoperative biogeometric computations, has been difficult to implement as the same is normally based, in large part, upon the adroitness of the individual practitioner. As a result, unacceptable variances between the surgically corrected bone and the ideally corrected bone, as determined by means of the aforenoted pre-operative computations, sometimes occur. Such variations, of course, must then either be rectified or compensated for by means of additional operational procedures in order to achieve the ideally corrected bone structure, or alternatively, may simply be permitted to exist without any further modifications being implemented. Either course of action is deemed unacceptable and undesirable from the patient's viewpoint.

The formation of the aforenoted wedge-shaped bone sections, and the severance and removal thereof, is normally achieved by several well-known means, e.g. conventional power saws, burrs or osteotomes; however, each of these means has inherent disadvantages of operative drawbacks. All of such means exhibit the shortcoming of not being readily able to accurately reproduce the desired wedge-shaped bone section in accordance with pre-operative considerations, and in addition, it has also been found that power saws often generate excessive heat which deleteriously affects the bone.

Circular saws have also, in the past, been utilized to form circular or crescentric cuts 10 in the bone, as shown in FIG. 1; however, the operational drawback of such a procedure has been the absolute necessity for the relative fixation of the bone components, which is normally achieved through means of pins or screws, due to the inherent alignment or orientation instability in the lateral direction characteristic of such cuts. The employment of such cutting devices, and the creation of the aforenoted cutting patterns, also does not permit the bone sections to be accurately aligned or oriented with respect to one another in three orthogonal planes, or in other words, with six degrees of freedom. Still further, with the use of circular saws, the resulting kerf is often inaccurate. In instances where the overall length of the bone is critical, an inaccurate kerf can deleteriously affect the proper location or disposition and operative functioning of the bone.

With the utilization of the foregoing wedge-creation techniques, the instability problems characteristic of the circular or crescentric techniques are overcome. However, conventional wedge-creation techniques exhibit other formidable problems. As shown in FIG. 2, the wedge section 12 is adapted to be removed from the bone 14, and it is particularly noted that the transverse dimension of the wedge section 12 is less than that of bone 14 so as to define a bone section 16 which is intact and residually integral with upper and lower bone sections 18 and 20, respectively. In this manner, section 16 ideally serves, in effect, as a hinge mechanism, e.g. so as to permit upper bone section 18 to be moved in the clockwise direction whereby the severance surfaces 22 and 24, originally defining wedge section 12 which has now been removed, may be mated. In this manner, the space which housed wedge section 12 is able to be closed, and as a result, upper bone section 18 may be re-aligned or re-oriented with respect to lower bone section 20 so as to achieve the ideal bone configuration or orientation.

While the aforenoted wedge-section techniques appear practicable, in actuality residual bone section 16 is often inadvertently fractured. Such circumstances obviously present considerable problems to the surgeon during surgery as well as to the patient. Still further, in practicing such wedge-section techniques, the bone sections 18 and 20 must be relatively fixed with respect to each other, and such a fixation process involves a considerable expenditure of time, is quite tedious to accomplish and requires a great amount of skill on the part of the surgeon. More particularly, as seen in FIG. 2, the osteotomy site is provided with a plurality of bore holes 26 which are drilled through the bone 14 upon opposite sides of wedge section 12. Wires or clasps (not shown) are then inserted through the holes and are suitably secured therein.

The cuts defining wedge section 12 may be made by means of a planar, chisel-type osteotome which eliminates the risk of exposing the bone to excessive heat, as is characteristic of power saws, or alternatively, the same could also be accomplished through means of burrs. The latter, however, as in the instance of power saws, do create excessive heat which tends to burn the bone sections; in addition, burrs are relatively unreliable for producing accurate cuts. This is particularly true if the same encounter variants of osseous tissue, which causes the burrs to exhibit skip positioning characteristics, e.g. as a result of the wedge section being necessarily defined within the medullary canal section of the bone. The preferred area of the bone within which the wedge section is defined is thus seen to be the cancellous portion of the head or base of the bone. Lastly, it is also noted that in employing both planar osteotomes or burrs, the ideal and accurate positioning of the bone sections with six degrees of freedom is also not achieved.

Another prior art technique which seeks to correct foot bone deformities by means of surgical procedures employs an osteotome which is V-shaped in transverse cross-section. This device has been particularly useful in the treatment of IPKs (intractable plantar keratoses) of the lesser metatarsals and, as can been seen in FIG. 3, the osteotomy site extends the full width of the bone 14. While the cutting of the bone can be accomplished by means of suitable saws or burrs, the V-osteotome is faster, easier to manipulate and more accurate in its resulting cuttings as both legs of the V-shaped cut are severed at the same time so as to be defined at predetermined locations relative to one another.

While the V-shaped osteotome has thus found particularly widespread use in the flotation of the metatarsals, the use of such an instrument is nevertheless considerably limited because the bone sections 18 and 20 are fixed relative to one another in the lateral direction as a result of the interlocking V-sections of such bones. This inherent lateral stability thus prevents the bone sections from experiencing six degrees of freedom. In addition, there is no means providing for an accurate adjustment of the bone sections relative to one another when, for example, a portion similar to the aforenoted wedge-section, of one of the bone sections is to be removed so as to correct the foot bone deformity. Thus, the employment of such an osteotome does not prove beneficial in performing the type of surgery required to correct the bone deformities of the type described hereinabove and exemplified in FIG. 2.

OBJECTS OF THE INVENTION

Accordingly, it is a general object of the present invention to provide a new and improved osteotome and a method of performing a surgical operation in order to correct bone deformities.

Another object of the present invention is to provide a new and improved osteotome and a method of performing a surgical operation which permits marking and/or cutting of bones to be severed in an extremely accurate manner so as to achieve an ideal correction of a bone deformity.

A further object of the present invention is to provide a new and improved osteotome and a method of performing a surgical operation whereby the severed bones may be accurately repositioned or reoriented relative to one another so as to achieve an ideal correction of a bone deformity.

An additional object of the present invention is to provide a new and improved osteotome and a method of performing a surgical operation whereby, for example, in achieving a particular type of correction of a bone deformity, a precisely configured wedge-type section of a bone may be removed so as to facilitate the accurate repositioning or reorientation of the remaining bone section relative to one another so as to achieve an ideal correction of a bone deformity.

Yet another object of the present invention is to provide a new and improved osteotome and a method of performing a surgical operation whereby the severed bone sections may be accurately repositioned or reoriented relative to one another by movement of the same within three orthagonal planes, or in other words, by imparting to such bone sections six degrees of freedom of movement.

A still further object of the present invention is to provide a new and improved osteotome which is structurally simple and easy to manipulate such that the operative procedures employing the same may be simply and rapidly performed.

An additional object of the present invention is to provide a new and improved osteotome which serves to sever the bone sections in a peculiarly novel manner so as to accurately remove a portion of the original bone and to impart inherent stability to the severed, residual bone sections relative to one another, whereby the remaining bone sections may be accurately aligned or oriented with respect to one another.

SUMMARY OF THE INVENTION

The foregoing and other objects of the present invention are achieved through the provision of an osteotome which includes a primary arcuate cutting blade portion and an auxiliary arcuate cutting blade portion, the portions being defined from congruent circles. A planar cutting blade is integrally connected to the auxiliary arcuate portion, and the axial extent of the planar and auxiliary cutting blades is less than that of the primary blade. In this manner, when cutting bones, the axially elongated primary portion can be retained within a first distinct cut of the bone while the osteotome is rotated to a second cutting position. The two distinct cuts are thus precisely aligned, and the planar blade serves to sever a wedge portion from the bone. The provision of the axially shortened auxiliary blade facilitates rotational movement and reorientation of the osteotome in either direction relative to the initial cut location. The planar cutting blade may have alternative configurations, and various visual indicating devices may be provided upon or in conjunction with the osteotome in order to facilitate the precise rotational movement or reorientation of the same between the first and second cutting positions.

BRIEF DESCRIPTION OF THE DRAWINGS

The above and other objects, features, and advantages of the present invention will be more fully appreciated as the same becomes better understood from the following detailed description when considered in connection with the accompanying drawings, in which like reference characters designate like or corresponding parts throughout the several views, and wherein.

DETAILED DESCRIPTION

Figure 1:
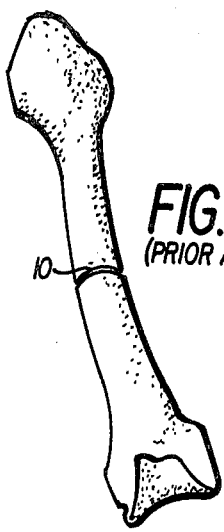
FIG. 1 is a schematic view of a prior art crescentric cutting of a bone.
Figure 2:
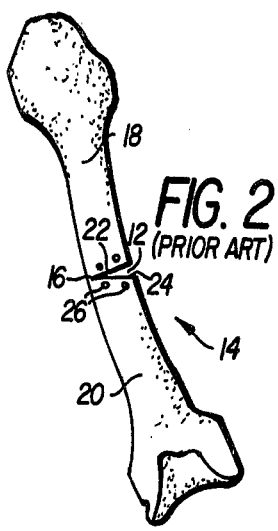
FIG. 2 is a schematic view of a prior art wedge-cutting of a bone.
Figure 3:
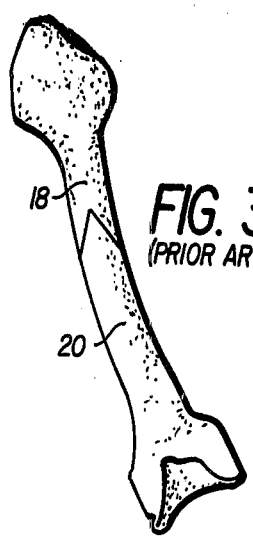
FIG. 3 is a schematic view of a prior art V-shaped cutting of a bone.
Figure 4:
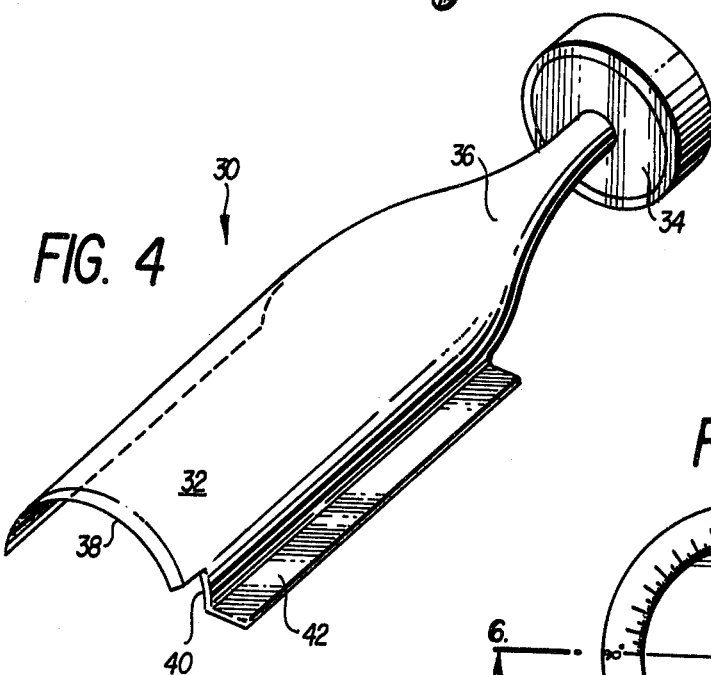
FIG. 4 is a perspective view of an osteotome constructed in accordance with the present invention and showing its cooperative parts.

Referring now to the drawings and more particularly to FIG. 4 thereof, the osteotome of the present invention is generally indicated by reference character 30 and includes a cutting blade portion 32 which is provided upon one end thereof, a head portion 34 which is provided upon the opposite end thereof, with an intermediate shaft portion 36 being defined between the blade and head portions and serving to integrally interconnect the same. More particularly, the blade, shaft and head portions of the instrument may either be of a one-piece construction, or alternatively, may be fabricated individually and fixedly secured together by suitable means.

Figure 7:
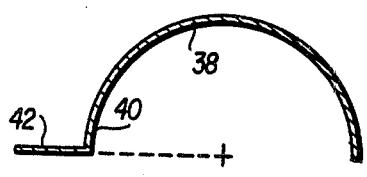
FIG. 7 is a schematic, cross-sectional view of the osteotome of the present invention.

As can best be appreciated from FIGS. 4 and 7, blade portion 32 comprises a primary arcuate cutting blade section 38, as viewed in cross-section, and an auxiliary arcuate cutting blade section 40, as well as a planar cutting blade section 42. Arcuate sections 38 and 40 are defined by loci which form parts of congruent perfect circles; it will be noted that the only difference between such sections resides in the fact that section 40 is defined along the arcuate surface of blade portion 32 at an axial postion displaced toward the head end of the instrument. Planar cutting blade 42 is preferably disposed along a radius of the circular locus defining blade sections 38 and 40, i.e. is perpendicular to a plane tangential to the outer surface of arcuate section 40 and passing through the intersection of sections 40 and 42. The axial extent of planar blade section 42 at the cutting blade end thereof corresponds to that of arcuate section 40, and consequently, sections 40 and 42 together define a stepped blade section relative to primary blade section 38, for a purpose to be described more fully hereinafter.

Figure 5:
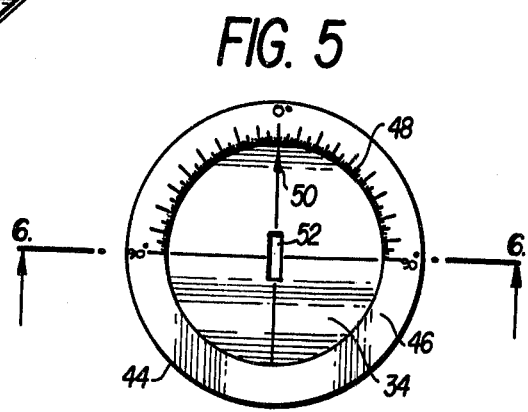
FIG. 5 is a plan view of the osteotome of FIG. 4.
Figure 6:
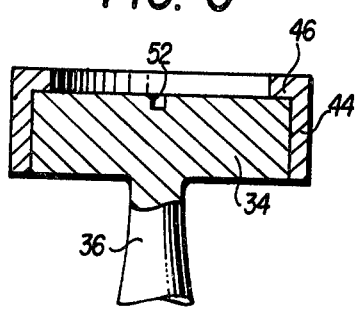
FIG. 6 is a cross-sectional view of the osteotome of FIG. 5 taken along the line 6—6' of FIG. 5.

With additional reference to FIGS. 5 and 6, head 34 has a cylindrical or disc-type configuration and, together with shaft 36, forms a T-shaped portion, in cross-section, of the instrument. An annular collar 44 is rotatably disposed about head 34 and, as best seen from FIG. 6, the height of collar 44 is greater than that of head 34 such that the former extends above the latter, the bottom annular surfaces of each member being substantially flush with each other. The upper portion of collar 44 is also provided with a radially inwardly projecting annular flange portion 46 which overlies the outer peripheral upper surface portion of head 34, in this manner, head 34 is, in effect, recessed downwardly within collar 44.

The inner peripheral surface of flange portion 46 is preferably provided with degree graduations 48 over a semicircular extent thereof and in conjunction therewith the upper planar surface of head 34 is provided with a pointed marker 50. A rectangular slot 52 is defined within the central portion of the upper planar surface of head 34. In this manner, a tool, e.g. a screwdriver blade (not shown) may be inserted within slot 52 and while the collar 44 is grasped, the tool may be rotated so as to rotate head 34, as well as integral instrument portions 36 and 32, relative to collar 44. Marker 50 will then indicate, relative to the degree graduation 48 defined upon collar 44, the angular extent through which the instrument 30 has been rotated in order to accomplish the purposes of the present invention.

Figure 8:
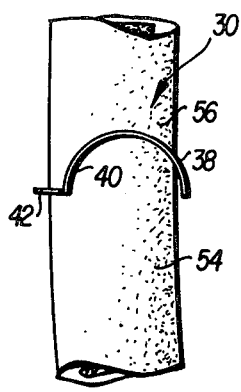
FIG. 8 is a schematic plan view showing the use of the osteotome of the present invention in cutting a bone.

In using the instrument of the present invention in performing an osteotomy, the instrument is disposed relative to the bone 54 to be served, e.g. as schematically illustrated within FIG. 8. For best results, the instrument 30 should ideally be substantially perpendicular to a medial plane of the bone which passes through the longitudinal axis of the bone and which is parallel to the supporting surface upon which the bone is to be supported during the surgical procedures. In other words, the instrument perferably should not be disposed at an angle to such plane along longitudinally and transversely extending planes. If the circumstances do dictate such an angular disposition, the same should preferably be limited to a range of $0° \leq 30°$.

As can also be appreciated from FIG. 8, the relative lateral or transverse extents of the arcuate blade sections 38-40 and planar blade section 42 is not critical, however, the same should be sufficient such that the outer portions of the blades 38 and 42 extend beyond the outer portions of the bone 54, as viewed in the lateral or transverse direction. This insures the fact that the bone 54 is in fact severed along its entire lateral or transverse extent and, in addition, that a relatively sharp bone section 56 is not produced within the area encountered by the free end of primary blade 38. In this manner, the risk of rendering such section 56 of the bone brittle and capable of being easily chipped or fractured is eliminated.

Figure 10:
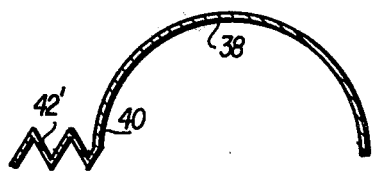
FIG. 10 is another embodiment of an osteotome of the present invention.
Figure 11:
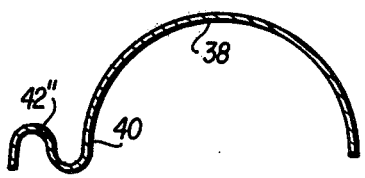
FIG. 11 is still another embodiment of an osteotome of the present invention.

Still further, while the configuration of the blade section 42 has been illustrated in FIGS. 4, 7 and 8 as being planar, the same may alternatively have a non-planar, e.g. jagged or corrugated configuration as illustrated in FIG. 10, or a sinusoidal or French curve type configuration as illustrated in FIG. 11. As was the case of planar blade 42, the blades of FIGS. 10 and 11 extend relative to arcuate sections 38 and 40 such that a medial plane of the blades, disposed parallel to the upper and lower surfaces of the blades as viewed in the Figures, is disposed along a radius of the circular loci defining sections 38 and 40. With the blade configurations of FIGS. 10 and 11, increased severance areas of the bones are defined and consequently, when the bone sections are reunited, healing of the same will be promoted.

In performing the osteotomy, prior to the initial cutting of the bone, a suitable buffer element is interposed between the underlying bone surface and the correspondingly disposed muscles, tissues or the like, in order to prevent severance thereof when the instrument of the present invention is forced downwardly so as to sever the bone as desired. After the disposition of such a buffer element, the instrument 30 is held relative to the bone as schematically illustrated in FIG. 8, and a suitable blunt instrument, e.g. of the mallet or hammer type, is brought down upon the head end of the instrument so as to force the cutting blades 38, 40 and 42 of the instrument to sever the bone. The initial cut of the bone is schematically illustrated in solid lines in FIG. 9.

It is also to be noted that prior to the initial cutting of the bone, the instrument is angularly disposed relative to the bone such that when the same is positioned as illustrated within FIG. 8, the head 34 of the instrument, and particularly the marker 50 thereof, is likewise disposed relative to collar 44 such that marker 50 is at the 0° mark thereof and aligned with the longitudinal axis of the bone. Consequently, when performing a second cutting of the bone, as illustrated in dotted lines in FIG. 9, in order to remove a wedge section 58 therefrom, the same may be performed by rotating the instrument through a predetermined angular displacement as dictated by marker 50 and collar 44 so as to precisely achieve the desired wedge-cut bone section. The angular displacement through which the tool is to be rotated may be predetermined in accordance with pre-operative calculations performed by the surgical team when reviewing the patient's case history and x-rays; consequently, such desired or theoretical angular displacement may be practically achieved with the instrument of the present invention. The rotation of the instrument relative to collar 44 can be accomplished, as aforenoted, through means of disposing a tool blade (not shown) within slot 52 of instrument head 34 and rotating the same or collar 44 while maintaining the other stationary.

Figure 9:
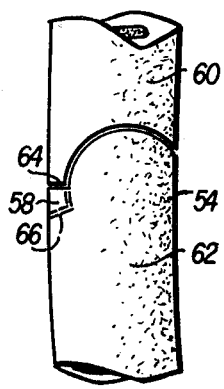
FIG. 9 is a schematic plan view of a bone which has been cut using the osteotome of the present invention.

As will be particularly appreciated from FIGS. 4 and 9, arcuate portions 38 and 40 are defined from loci of perfect circles. Thus, when the instrument 30 is to be rotated from its initial position corresponding to the initial cut position to its subsequent posiition angularly removed from the initial position so as to perform the second cutting, such circular loci sections of the instrument cause the instrument to be rotatably fixed in position with respect to the bone sections and to sever bone sections, along with planar blade portion 42, which precisely correspond with one another. In this manner, when wedge section 58 of the bone is removed, the upper section 60 of the bone 54 may be rotated relative to lower section 62 of bone 54, or vice versa, whereby the planar mating severed surfaces 64 and 66 may in fact be mated together in a precise fit.

It is also to be noted that in performing the two cuttings of the bone, the instrument is withdrawn somewhat after the initial cut has been made, so as to permit blade sections 40 and 42 to clear the bone while retaining arcuate section 38 embedded within the cut. This is facilitated by forming sections 40 and 42 in the aforenoted stepped manner relative to section 38. The latter thus serves as a pivoting mechanism for facilitating the precise rotation of the instrument, as noted hereinabove, when angularly repositioning the instrument from the first cut position to the second cut position. The transverse width of arcuate section 40 along the arcuate extent thereof is predetermined so as to facilitate angular movements which are normally required in performing the surgery of the aforenoted type. If such recessed or stepped portion of section 40 were not provided, but to the contrary, the axial extent of the same corresponded to that of section 38 with the axial extent of section 42 remaining as illustrated, then the instrument could not be rotated in either direction when repositioning the same from the first cut position to the second cut position, but rather it could only be rotated in the angular direction proceeding from blade section 42 to arcuate section 38 after the instrument had been withdrawn somewhat in order for blade 42 to clear the bone. In accordance with this feature peculiar to the present invention, rotation in either direction is facilitated. In order to provide for such the accurate angular positioning of the instrument, 90° graduated scale guadrants are provided upon collar 44 at opposite sides of the 0° mark.

Figure 12:
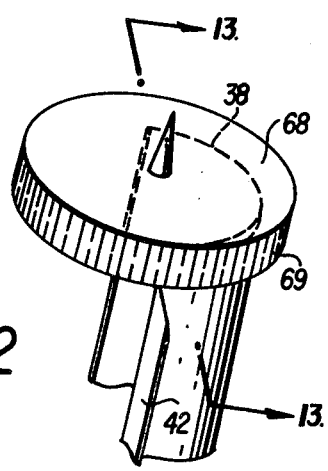
FIG. 12 is a perspective view of an indicating cap which may be used in conjunction with the osteotome of the present invention.
Figure 13:
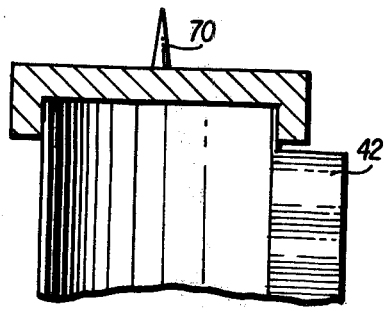
FIG. 13 is a cross-sectional view of the apparatus of FIG. 12 taken along the line 13—13 of FIG. 12.

In order to facilitate the precise determination of the required angular rotation of the instrument between the first and second cuttings of the bone, and in order to implement such rotation during the operative procedure, the instrument of the present invention may also be provided with a cup-shaped cap 68 which is adapted to be removably disposed upon the cutting blade end of the instrument, as best seen in FIGS. 12 and 13. The outer peripheral surface of the cap is, similarly to collar 44, provided with a graduated degree scale 69, and the interior periphery of cap 68 is just slightly larger than that of arcuate section 38 so as to envelope the same. A bottom portion of cap 68 rests upon the cutting blade edge of blade section 42, while the outer planar surface of the cap has a pin 70 projecting upwardly from the central portion thereof.

In predetermining the size of the wedge portion 58 of the bone to be removed during preoperative procedures, the cap 68 may be mounted upon the instrument and the same inverted so as to permit the cap to be mounted upon the preoperative x-rays by means of the pin 70 piercing same. As the graduated scale 69 will then be disposed immediately above the x-ray, the angular extent of the wedge section 58 may be readily determined by correlating the x-ray to the scale 69. During the operative procedure as the angular extent of such wedge section has thus already been predetermined, and the instrument 30 may be appropriately manipulated in correspondence thereto, i.e. the same may be rotated through the predetermined angular extent, as now determined by means of marker 50 and collar 44, the scale graduations upon collar 44 corresponding to those upon cap 68.

Figure 14:
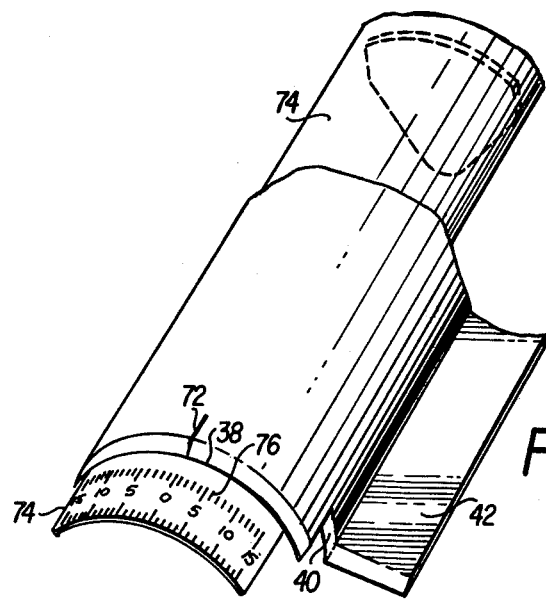
FIG. 14 is a perspective view of another embodiment of an osteotome of the present invention.

As a further means of facilitating the precise angular orientation of the cutting blades between the initial and second cutting positions, the apparatus of FIG. 14 may likewise be employed. In accordance with this apparatus, the forward end of blade section 38 is provided with an indicating mark 72 and has disposed interiorly thereof, in an enveloping concentric manner, an arcuate plate 74 upon which degree graduations 76 are provided. The plate 74 is slidably disposed relative to blade 38 in the longitudinal direction of the instrument and is likewise rotatably disposed relative to blade 38 in the transverse direction. When the initial cut of the bone is to be performed, the plate 74 is retracted longitudinally to a sufficient extent such that the same does not interfere with the cutting operation of the blades 38, 40 and 42. Subsequent to the performance of the initial cut, the instrument is withdrawn from the initial cut and plate 74 is then longitudinally moved so as to emerge from its enveloped position. Plate 74 is now disposed within the initial cut in precisely the same position that the cutting blade 38 was disposed and the indicator 72 of blade 38 is then aligned with the 0° graduation of scale 76. In accordance with pre-operative considerations, the instrument is then rotated through the predetermined angular orientation such that the mark 72 of blade 38 is at the predetermined corresponding graduation of scale 76. This indicates the desired position for the second cutting of the bone, which is then performed.

Alternatively, plate 74 may be constructed as axially movable blade 38, in which event the length of blade 38 need not exceed that of sections 40 and 42 but only need be extended beyond the extent thereof during the procedure.

As can be appreciated from the foregoing, the present invention discloses a new and improved instrument and method for performing osteotomies whereby bone sections may be easily and accurately aligned with respect to one another. As the bone sections may be moved relative to one another in an arcuate manner, as well as orthagonally along the plane of the cut, the same may in fact move with six degrees of freedom while nevertheless being aligned with each other through means of the interfitted arcuate and substantially planar portions of the cuts as defined by the blade sections of the instrument.

The osteome of the present invention can further be used as a marking device for cuts to be performed by other means, e.g. a circular saw or laser.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An elongated osteotome capable of surgically cutting bones, comprising:
   cutting blade means at one end thereof including means for retaining said cutting blade means aligned relative to an initial distinct cut of said bone at a first position while said cutting blade means is repositioned to a second position so as to perform a second, distinct cut of said bone;
   said aligning means comprising an axially elongated portion of said cutting blade means which is arcuate in cross-sectional configuration and which extends to an edge of said cutting blade, at least part of said elongated portion remaining within said initial cut when said second cut is performed; means for permitting said cutting blade means to be rotatably repositioned along said bone, relative to said initial cut, to form said second distinct cut at said second position while maintaining said elongated portion within said initial cut, said cutting blade means including a cutting portion extending outwardly from said arcuate portion;
   whereby said two distinct cuts of said bone will be accurately aligned relative to each other.

2. An osteotome as set forth in claim 1, wherein said cutting blade means comprises:
   an axially extending arcuate cutting blade portion integrally connected with an axially recessed arcuate cutting portion, said outwardly extending portion integrally connected with said outwardly extending portion including a generally planar cutting blade axially recessed from said arcuate axially extending cutting blade portion and extending outwardly from said axially recessed arcuate portion whereby, when said blade means is moved from said first position to said second position and said first and second cuts are performed, an accurate wedge-shaped bone portion will be severed from said bone.

3. An osteotome as set forth in claim 1, wherein:
   said cutting blade means includes stepped means axially recessed from said axially elongated portion for facilitating the repositioning of said cutting blade means to said second position which is defined upon either side of said first position.

4. An osteotome as set forth in claim 1, wherein said cutting blade means comprises:
   an arcuate cutting blade and said outwardly extending portion which includes a radially extending corrugated cutting blade integrally connected together.

5. An osteotome as set forth in claim 1, wherein said cutting blade means comprises:
   an arcuate cutting blade and said outwardly extending portion which includes a radially extending sinusoidally-shaped cutting blade integrally connected together.

6. An osteotome as set forth in claim 1, further comprising:
   means for visually indicating the distance said cutting blade means is to move from said first position to said second position.

7. An osteotome as set forth in claim 6, further comprising a handle means wherein:
   a head portion is defined upon the other end thereof; said indicating means includes a collar, having a graduated degree scale defined thereon, rotatably disposed about said head; and said head has a marking device defined thereon for operatively cooperating with said collar scale.

8. An osteotome as set forth in claim 6, wherein said indicating means comprises:
   a cap secured upon the cutting end of said cutting blade means; a graduated degree scale defined upon the outer periphery of said cap; and
   means for securing said cap and said osteotome to preoperative diagnostic data material in order to directly correlate said scale with said data material.

9. An osteotome as set forth in claim 6, wherein said indicating means comprises:
   a plate, having means permitting longitudinal adjustment thereof with respect to said cutting blade means, said plate having a graduated degree scale defined thereon; and
   said cutting blade means has a marking device defined thereon for operatively cooperating with said plate degree scale.

10. In a surgical method for changing the axial alignment of a bone by severing said bone and healingly repositioning the resulting segments thereof with respect to each other, the improvement which comprises:
    cutting across a portion of said bone in an arc extending from and through one side of said bone and terminating between said side and the opposed side of said bone, said arc being the arc of a circle having a center which is offset from the longitudinal axis of said bone; and
    cutting two radially extending, circumferentially spaced cuts from said arc to an through said opposed side of said bone to form a removable wedge so that the resulting bone segments can be rotated along said arc to effect said repositioning thereof.

* * * * *